United States Patent [19]

Peterson

[11] 4,129,520
[45] Dec. 12, 1978

[54] SOAP MAKING

[75] Inventor: Donald J. Peterson, Cincinnati, Ohio

[73] Assignee: The Procter & Gamble Company, Cincinnati, Ohio

[21] Appl. No.: 731,183

[22] Filed: Oct. 12, 1976

[51] Int. Cl.$^2$ .................... C11D 13/00; C11D 15/04
[52] U.S. Cl. .................................. 252/367; 252/108; 252/122; 252/141; 252/41; 260/417; 260/419; 260/426
[58] Field of Search ............... 252/367, 108, 122, 141, 252/41, 369; 260/413–416, 417–418, 419, 426

[56] References Cited

U.S. PATENT DOCUMENTS 2,753,364  7/1956  Biner et al. ........................... 260/413

Primary Examiner—Mayer Weinblatt
Attorney, Agent, or Firm—Jerry J. Yetter; Julius P. Filcik; Richard C. Witte

[57] ABSTRACT

Alkali metal salts of organic acids are prepared by saponifying the corresponding organic acid ester with an alkali metal hydroxide in a liquid reaction medium comprising a substantially water-free alkyl nitrile.

16 Claims, No Drawings

SOAP MAKING

BACKGROUND OF THE INVENTION

The present invention encompasses methods for saponifying organic acid esters, including fatty acid glyceride esters. More specifically, organic acid esters are saponified with an alkali metal hydroxide in a liquid reaction medium comprising a substantially water-free alkyl nitrile to provide unsolvated alkali metal salts of the organic acids. When fatty acid esters are used in the process, dry alkali metal soaps are secured.

The preparation of alkali metal salts of organic acids by saponifying the corresponding organic acid esters, as in traditional soap making processes, is typically carried out using an alkali metal hydroxide base, the organic acid ester, and water as the reaction medium. Heretofore, such reactions have been energy intensive for at least two reasons. First, heat energy is required to initiate and sustain the saponification of the organic acid ester by the aqueous solution of the alkali metal hydroxide. Second, the organic acid salts are strongly solvated by the water from the aqueous reaction medium. Accordingly, some of the water must be removed to recover the organic acid salts, and heat energy is needed for this solvent removal step.

By the present invention, it has been discovered that substantially water-free alkyl nitriles provide a reaction medium wherein organic acid esters can be saponified with alkali metal hydroxides to provide the alkali metal salts of organic acids which precipitate from the reaction medium in an unsolvated form. Accordingly, solvent removal in the present process is not as energy intensive as in the aqueous process. Moreover, the present process is exothermic and, once initiated, proceeds essentially to completion without external heating. Soap making processes carried out in the manner of the present invention using fatty glycerides as the organic acid ester provide substantially dry, unsolvated soap powder in an extremely short period of time in exceptionally high yields.

RELATED REFERENCES

The art of preparing the alkali metal salts of organic acids, especially as it is embodied in soap making processes, is old and is the subject of a large body of literature. Anhydrous soap making processes have been disclosed heretofore, as have soap making processes which employ organic solvents as the reaction medium. The alkyl nitriles used as the reaction medium in the present process are well-known materials.

Despite the voluminous literature in this area and the long history of soap making and syntheses of fatty acid salts, the present process does not appear to have been contemplated heretofore.

Acetonitrile (methyl cyanide; cyanomethane; ethanenitrile) is a highly preferred alkyl nitrile solvent for use in the present process. As pointed out in THE MERCK INDEX, Seventh Ed., page 8, this material has been used to extract fatty acids from fish liver oils and other animal and vegetable oils. This material is also known as a medium for producing reactions involving ionization, as a solvent in non-aqueous titrations, and as a non-aqueous solvent for inorganic salts.

The use of acetonitrile as an extraction solvent for separating/removing various materials from compositions containing fatty acids, sterols, and the like, is disclosed in the following references: U.S. Pat. No. 2,681,922, Balthis, 6/22/54; U.S. Pat. No. 2,528,025, Whyte, 10/31/50; Chemical Abstracts 38 6180; 84 80436u; 48 6698; 57 13224; 47 3660; 60 2330; 49 15266; 54 5126; 50 14322; and 46 6468.

The use of propionitrile in various liquid phase extraction processes involving glycerides, fatty acids, and the like, is disclosed in U.S. Pat. No. 2,316,512, Freeman, 4/13/43; U.S. Pat. No. 2,200,391, Freeman, 5/14/40; U.S. Pat. No. 2,313,636, Freeman, 3/9/43; U.S. Pat. No. 2,390,528, Freeman, 12/11/45; and Canadian Pat. No. 488,250, Freeman, 11/18/52.

Processes for manufacturing modified oil products from fatty oils, for manufacturing soap compositions, and for preparing metallic salts of higher fatty acids, which are carried out under anhydrous conditions or with the use of organic solvents of various types are disclosed in the following references: U.S. Pat. No. 1,957,437, Auer, 5/8/34; U.S. Pat. No. 3,376,327, Freeland, 4/2/68; U.S. Pat. No. 2,271,406, Thurman, 1/27/42; U.S. Pat. No. 2,383,630, Trent, 8/28/45; U.S. Pat. No. 3,476,786, Lally and Cunder, 11/4/69; Chemical Abstracts 53 20838; 26 5875; 52 7743; and 53 20850.

Various miscellaneous references relating to the use of cyano compounds or amines of various types in the preparation of carboxylic acids and general references to the use of acetonitrile as a solvent are as follows: U.S. Pat. No. 2,042,729, Ralston and Poole, 6/2/36; U.S. Pat. No. 3,828,086, Kenney and Donahue, 8/6/74; U.S. Pat. No. 3,519,657, Olah, 7/7/70; U.S. Pat. No. 2,211,941, Sullivan, 8/20/40; U.S. Pat. No. 1,833,900, Hoyt, 12/1/31; U.S. Pat. No. 2,402,566, Milas, 6/25/46; U.S. Pat. No. 2,640,823, Gloyer and Vogel, 6/2/53; U.S. Pat. No. 2,895,974, Case, 7/21/59; and Chemical Abstracts 53 9642.

German Patentschrift No. 1,254,139, May 30, 1968, discloses a process for preparing saturated fatty acids by reacting an α-olefin with a stoichiometric excess of acetonitrile, or acetate reagent, in the presence of an organic peroxide It is clear that the use of the alkyl nitriles as an extraction/separation medium in the manner suggested by these references does not contemplate their use as a reaction solvent in the manner of the present invention. Moreover, the use of organic solvents, anhydrous conditions, or cyano compounds to prepare soaps, and the like, does not contemplate the present invention.

Attention is specifically directed to U.S. Pat. No. 3,133,942, Hahl, patented May 19, 1964, and U.S. Pat. No. 2,753,364, Boner and Breed, patented July 3, 1956. The U.S. Pat. No. 3,133,942 relates to the production of metal salts of organic acids and, as disclosed therein, is carried out by using an organic acid and certain metals in the form of metal powders. Inert organic solvents, including acetonitrile, propionitrile and benzonitrile, are disclosed for use in the process. The process differs from that of the present invention in that it uses neither alkali metal hydroxides nor organic acid esters as the starting materials. Moreover, many of the solvents disclosed as being useful in the U.S. Pat. No. 3,133,942 patent are not contemplated for use herein.

The Boner, et al., patent, above, relates to a method for manufacturing lithium soaps (lubricating greases) using lithium carbonate and free fatty acids as the starting materials. Acetonitrile, benzonitrile and "benzyl cyanide" are taught to be useful solvents in the process, along with many other organic solvents. It will be appreciated that this reference does not teach the use of alkali metal hydroxides, nor organic esters, especially glyceride esters, such as those used in the present invention; is almost unlimited as to the type of organic nitrogen-containing materials suggested for use as the solvent medium; and does not teach or suggest the present process which is limited to the alkyl nitriles which have now been discovered to be particularly advantageous when employed in the manner disclosed herein.

Attention is also directed to the review article *Khim. Prom.* (Moscow) 1968 44 (10) 722-6 (Russ.) which, in abstract form (C.A. 70 28299y), is said to relate to the use of MeCN as a solvent, its reactions with aldehydes, ketones, alcohols, dienes and organic acids, substitution reactions and with inorganic compounds, and which cites 90 references.

Attention is also directed to the review article by E. J. Fischer, *Allgem. Oel-u. Fett-Ztg.* 33, 78-81 (1936) which, in abstract form (C.A. 30 3539), is said to relate to methods for preparing acetonitrile and its use, principally as a solvent.

In addition to the foregoing, the co-pending application of Peterson, Ser. No. 731,163, filed Oct. 12, 1976, discloses a process for preparing the alkali metal salts of organic acids using organic acid esters, an alkyl nitrile as the liquid reaction medium, and concentrated aqueous solutions of alkali metal hydroxides.

The co-pending application of Peterson, Ser. No. 731,182, filed Oct. 12, 1976, discloses a process for preparing soaps and synthetic detergent compositions with a low water content using an energy sparing process which employs the dry soaps prepared in the manner of this invention.

The co-pending application of Peterson, Ser. No. 731,176, filed Oct. 12, 1976, discloses and claims a combination of alkyl nitriles and alkali metal hydroxides as super bases which are useful in various chemical processes.

SUMMARY OF THE INVENTION

The present invention encompasses a process for saponifying organic acid esters to their alkali metal salts. The process comprises saponifying the organic ester corresponding to the organic acid salt desired using an alkali metal hydroxide in a liquid reaction medium comprising a substantially water-free liquid alkyl nitrile compound.

The reaction herein can be carried out using glyceride esters, including the mixed mono-, di- and tri-glyceride esters derived from animal fats and oils and/or vegetable fats and oils. Such materials typically comprise fatty acid ($C_{10}$–$C_{20}$) esters and are well known for use in soap making processes. Accordingly, the process herein can be used to prepare water-soluble soaps, which are, typically, the alkali metal salts of $C_{10}$–$C_{20}$ organic acids.

The present process can also be carried out using lithium hydroxide and $C_{10}$–$C_{24}$ fatty acid esters, thereby securing lithium "soaps" which are especially useful and known in the art as lubricating greases.

The process herein is simply and economically carried out by admixing the alkyl nitrile reaction medium, the ester, and the solid alkali metal hydroxide (typically, pulverized) in a suitable container, initiating the reaction (typically, by gentle heating) and allowing the reaction to proceed. The reaction is exothermic and, once initiated, substantially self-sustaining. Heating can optionally be used to increase yields to the range of 95%–100%.

Soaps prepared in the foregoing manner simply precipitate from the reaction medium as an unsolvated, substantially white powder. Advantageously, much of the colored matter which is commonly present in commercial grades of animal fats and oils used as the ester starting material is retained in solution in the alkyl nitrile. Accordingly, an excellent soap product, substantially freed from color bodies, can be secured by the present process. Typical yields of soap are in the range of 90% in a matter of a few minutes.

DETAILED DESCRIPTION OF THE INVENTION

The present invention encompasses a process for preparing the alkali metal salts of organic acids which comprises saponifying the corresponding organic acid ester with an alkali metal hydroxide in a liquid reaction medium comprising a substantially water-free alkyl nitrile. The organic acid esters employed herein can be simple alkyl or aryl esters, or can be glyceride esters such as the triglycerides which typically constitute the major proportion of the materials present in fats and oils derived from animal or vegetable sources. The reaction herein can be used, for example, to prepare lubricating greases by saponifying $C_{10}$–$C_{24}$ organic acid esters with lithium hydroxide. The present process can also be employed to prepare water-soluble detersive surfactants, i.e., soap, by saponifying esters of organic acids having chain lengths in the range of about $C_{10}$–$C_{20}$. The reaction does not appear to depend on the nature of the acid ester used; hence, alkali metal salts of organic acids having chain lengths shorter or longer than mentioned above, as well as branched chain and aryl organic acids, can also be prepared in the manner of this invention.

By "alkali metal salts of organic acids" herein is meant compounds of the formula RCOOM, wherein the RCOO— group is an organic acid substituent, unlimited in the type of R group, and wherein M is an alkali metal.

By "organic acid ester" herein is meant a compound of the formula RCOOR', wherein RCOO— is as above, and wherein group R' is an organic substituent group derived from an alcohol or polyol, unlimited in type.

By "alkali metal hydroxide" herein is meant lithium hydroxide, sodium hydroxide, potassium hydroxide, rubidium hydroxide, and cesium hydroxide. Sodium hydroxide and potassium hydroxide are especially useful for making water-soluble soaps for detergent use. Lithium hydroxide is especially useful for preparing lubricating greases.

By "alkyl nitrile" herein is meant a compound of the formula R"CN, wherein R" is a linear, branched chain or cyclic aliphatic substituent. Typical examples of such materials are acetonitrile and propionitrile, which are preferred for use herein. Aromatic nitriles, e.g., benzonitrile, have been found not to be useful as a reaction medium and are not encompassed by the present invention. Acetonitrile is the most highly preferred alkyl nitrile for use herein.

By "substantially water-free" herein is meant that water is not intentionally added to the alkyl nitrile reaction medium. Some water may be present in the reaction medium, but this usually only constitutes a small percentage (<ca. 10%) in the reaction medium. For example, the alkali metal hydroxides, especially LiOH, which is commercially available as the monohydrate, are somewhat hygroscopic and carry some moisture into the system.

By "glycerides" herein is meant organic acid esters of glycerol. The term glycerides encompasses mono-, di- and triglycerides, since glycerol is a trihydric alcohol which can be esterified on any, or all, of the three hydroxyl groups. Triglycerides constitute the major components of naturally-occurring fats and oils which are typically used as starting materials in soap making processes.

By "animal or vegetable fats and oils" herein is meant the organic acid glyceride materials which can be secured from a wide variety of sources. Specific, nonlimiting examples of such materials include lard, tallow, coconut oil, palm oil, various by-products from animal rendering operations, oils from oleaginous seeds such as the soybean, sunflower seeds, and the like, cottonseed oil, etc. Typical listings of such materials are widely available, and all such glyceride mixtures are useful in the present process.

By the term "comprising" herein is meant that various other, compatible ingredients can be present in the reaction medium as long as the critical reactants and alkyl nitrile are present. The term "comprising" thus encompasses and includes the more restrictive terms "consisting of" and "consisting essentially of" which can be used to characterize the essential materials (ester, alkali metal hydroxide and alkyl nitrile) used herein.

All percentages herein are by weight, unless otherwise specified.

The process herein is carried out by simply admixing the carboxylic acid ester to be saponified with the alkyl nitrile and the alkali metal hydroxide in any suitable reaction vessel. The reaction can be initiated by gently heating the mixture, if desired. However, the saponification reaction of this invention will generally initiate spontaneously on stirring of the reactants for a few minutes. When using carboxylic acid esters which are especially easily saponified (e.g., nitrophenyl esters) the reaction is self-initiating almost immediately and proceeds to substantially 100% completion in the matter of a few minutes, or less.

It is to be understood that the alkali metal hydroxide employed herein is not particularly soluble in the alkyl nitrile reaction medium. Apparently, some alkali metal hydroxide does dissolve in the alkyl nitrile and saponifies an equivalent amount of the organic acid ester, whereupon additional alkali metal hydroxide dissolves, etc. For this reason, it is preferred to use alkali metal hydroxides which have been ground to an appropriate particle size to aid in dissolution in the alkyl nitrile. This is not critical to the invention herein, but only makes the reaction more convenient. For general purposes, the alkali metal hydroxide can be pulverized to a particle size that passes through a 50 mesh sieve and used herein.

The nature of the fatty acid esters employed herein is not critical to the practice of this invention. Accordingly, the ester of any fatty acid or substituted fatty acid species with any alcohol or substituted alcohol species provides starting materials which can be used herein. It will be appreciated, of course, that some esters will react more rapidly than others. However, the present process has been found to be useful for saponifying even substantially inert esters such as the sucrose fatty octaesters, which demonstrates the exceptional efficacy of this reaction as a saponification process.

In the practice of this invention it is convenient to employ a stoichiometric amount of the alkali metal hydroxide and ester to be saponified. For most purposes, an excess of the alkali metal hydroxide is employed to ensure that the reaction is carried to completion and that no ester is wasted. The alkyl nitrile is generally used in a solvent amount, i.e., sufficient to dissolve the acid ester. In some instances, the acid ester may not be entirely soluble in the alkyl nitrile and a ternary, heterogeneous reaction mixture of alkali metal hydroxide/alkyl nitrile/acid ester is formed. It does not appear to be necessary for the reaction mixture to be homogeneous, and excellent yields of the alkali metal salts of fatty acids are secured even under such conditions.

In an alternate mode, an excess of ester is used, and the mixture of any unreacted ester and alkyl nitrile is simply re-used with fresh alkali metal hydroxide in subsequent processes. This avoids the need for any acid neutralization step to remove excess base during soap recovery.

It will be appreciated that small amounts (usually less than about 10% of the alkyl nitrile) of extraneous organic solvents and/or water may contaminate the reaction systems used in any commercial scale soap making process. Excessive amounts of such extraneous materials may cause an undesirable dilution of the alkyl nitrile/alkali metal hydroxide base medium. Moreover, solvents which are miscible with the alkyl nitrile may solvate the alkali metal hydroxide and diminish the overall reactivity of the system. Thus, the presence of excessive amounts of extraneous materials is preferably avoided herein to assure that the special advantages of the process are obtained.

The saponification reaction of this invention is conveniently carried out at a weight ratio of organic acid ester:alkali metal hydroxide:alkyl nitrile in the range of from about 1:0.1:1 to about 1:1:5, but other ratios can be used, as desired.

After recovery of the reaction product by filtration, air drying can be used to remove any entrained alkyl nitrile.

The following examples illustrate the practice of this invention, but are not intended to be limiting thereof.

EXAMPLE I

Reaction of Triglycerides With Anhydrous Sodium Hydroxide

To a mixture of 50 g. (0.067 mole) of a 50:50 mixture of tallow and coconut fats in 250 mls. of acetonitrile at a temperature of 75° C., was added 8.15 g. (0.20 mole) of finely powdered 98% sodium hydroxide. The reaction was exothermic and refluxed vigorously, without extraneous heating, about two minutes after the addition of the sodium hydroxide. The reaction mixture was stirred at reflux temperature for a total of five minutes. During this time, a layer of fine, white, solid powdered material formed in the reaction vessel.

The solid material was collected by filtration and air dried overnight to give a yield of 46 g. (88%) of the sodium carboxylates (soaps) corresponding to the fatty acids in the starting material triglycerides.

In the process of Example I the acetonitrile is replaced by an equivalent amount of benzonitrile ($C_6H_5CN$) and no apparent reaction occurs.

In the process of Example I the fats are reacted with less than a stoichiometric amount of sodium hydroxide to provide "super-fatted" soap.

EXAMPLE II

Reaction of Tallow and Coconut Triglycerides With Sodium Hydroxide

To a stirred mixture of 100 g. (0.125 mole) of 80% tallow-20% coconut triglycerides and 500 mls. of acetonitrile at 60° C. was added 16.3 g. (0.40 mole) of finely powdered 98% sodium hydroxide. The reaction mixture was stirred for three hours. Intermittent heating was used to maintain a reflux temperature (80° C.-82° C.).

The foregoing reaction mixture was filtered hot and the filter cake washed twice with 100 ml. portions of acetonitrile. The resulting white solids were air dried overnight to give 100 g. (97%) of the sodium salts of the fatty acids from the mixed triglycerides.

The acetonitrile solution was evaporated to a residue of 14 g. From this residue, 5.9 g. (51%) of glycerine was recovered by vacuum distillation.

As can be seen from the foregoing, the soap making process of the present invention gives yields on the order of 90%, or, if external heating is used in addition to the heat generated by the reaction process, yields on the order of 97% can be secured.

EXAMPLE III

Preparation of Potassium Myristate

To a solution of 12.2 g. (0.05 mole) of methyl myristate in 120 mls. of acetonitrile was added 3.3 g. (0.05 mole) of finely pulverized 85% potassium hydroxide. The reaction mixture was stirred at substantially room temperature and monitored by following the rate of disappearance of methyl myristate by gas phase chromatographic analysis. After six hours, methyl myristate was no longer detectable. The precipitated sodium myristate was isolated by vacuum filtration and air dried overnight. A yield of 12.8 g. (96%) of solid potassium myristate product was secured.

In the process of Example III, the KOH is replaced by an equivalent amount of LiOH, NaOH, RbOH and CsOH, respectively, and the respective alkali metal soaps are secured.

The process of Example III is carried out with the acetonitrile being replaced by an equivalent amount of propionitrile, butyronitrile, n-pentylnitrile and cyclohexylnitrile, respectively, and equivalent results are secured. Saponification reactions carried out using the higher alkyl nitriles (greater than about $C_6$ alkyl) are much slower than with the preferred lower alkyl nitriles.

EXAMPLE IV

Preparation of Lithium Carboxylate

To a suspension of 50 g. (0.054 mole) of hydrogenated castor oil in 250 mls. of acetonitrile at 70° C. was added 6.8 g. (0.162 mole) of lithium hydroxide monohydrate. The reaction mixture was stirred for 21 hours at reflux (81° C.). The product which precipitated from solution was isolated by vacuum filtration of the hot reaction mixture and was dried in a vacuum desiccator. Product yield was 49 g. (98%) of the corresponding lithium carboxylate, predominately 12-hydroxystearate, lithium salt.

EXAMPLE V

Preparation of Bar Soap

The substantially anhydrous soap prepared in the manner of Example I herein is in a phase which is useful, once hydrated, to form bar soaps in the ordinary manner, as follows.

| Ingredient | Wt. % |
|---|---|
| Soap (Na form)* | 79.0 |
| Coconut Oil Fatty Acids | 7.0 |
| Sodium Chloride | 1.0 |
| $TiO_2$ | 0.25 |
| Water | 10.75 |
| Minors** | Balance |

*Prepared in the manner of Example I
**Perfume, coloring, perfume stabilizer

A composition of the foregoing type is extruded through a standard soap making extruder and formed into bars, using commercial bar soap processing techniques. An excellent soap bar product which compares favorably with commercially available soaps and comprising about 10% by weight water is secured.

The anhydrous soaps prepared in the manner of this invention are in a convenient granular form and are particularly adapted for use in mechanical dispensers, such as those found in public lavatories.

EXAMPLE VI

Saponification of Dimethyl Adipate 17.4 g. (0.1 mole) of dimethyl adipate were dissolved in 100 mls. of acetonitrile and heated to 70° C. 8.2 g. (0.2 mole) of 97% pure sodium hydroxide were added to the reaction mixture as a fine powder (50 mesh). The reaction mixture was stirred at reflux temperature for 18 hours. The resulting solution was filtered hot and the solids were air dried to yield disodium adipate as the reaction product.

The foregoing illustrates that the process herein is useful for saponifying diacid esters.

What is claimed is:

1. A process for preparing the alkali metal salts of organic carboxylic acids which comprises saponifying the corresponding organic carboxylic acid ester of the formula RCOOR' wherein RCOO- is an organic acid substituent and wherein R' is derived from alcohols or polyols, with an alkali metal hydroxide selected from lithium hydroxide, sodium hydroxide, potassium hydroxide, cesium hydroxide and rubidium hydroxide in a liquid reaction medium comprising a substantially water-free alkyl nitrile of the formula R"CN wherein R" is selected from linear, branched chain, and cyclic aliphatic substituents; separating said salts from the reaction mixture; and removing excess alkyl nitrile from the salts.

2. A process according to claim 1 wherein the alkali metal hydroxide is a member selected from the group consisting of lithium hydroxide, sodium hydroxide, and potassium hydroxide.

3. A process according to claim 1 wherein the alkyl nitrile is a member selected from the group consisting of acetonitrile and propionitrile.

4. A process according to claim 1 wherein the organic carboxylic acid ester is a glyceride ester selected from monoglyceride, diglyceride and triglyceride esters of glycerol and organic carboxylic acids.

5. A process according to claim 4 wherein the glyceride ester is a triglyceride.

6. A process according to claim 1 for preparing lubricating greases comprising saponifying an organic acid ester wherein the organic acid substituent is a $C_{10}$–$C_{24}$ organic acid substituent with lithium hydroxide in a substantially water-free alkyl nitrile reaction medium selected from acetonitrile, propionitrile, butyronitrile, n-pentylnitrile, and cyclohexylnitrile.

7. A process according to claim 6 wherein the organic carboxylic acid ester is a glyceride ester selected from monoglyceride, diglyceride and triglyceride esters of glycerol and $C_{10}$–$C_{24}$ organic carboxylic acids.

8. A process according to claim 7 wherein the glyceride ester is a triglyceride.

9. A process according to claim 6 wherein the alkyl nitrile is a member selected from the group consisting of acetonitrile and propionitrile.

10. A process according to claim 6 wherein the alkyl nitrile is acetonitrile and wherein the ester comprises and mixed glyceride esters derived from animal fats and oils or vegetable fats and oils.

11. A process according to claim 1 for making soap comprising saponifying an organic carboxylic acid ester wherein the organic acid substituent is a $C_{10}$–$C_{20}$ organic acid substituent with sodium hydroxide or potassium hydroxide in a liquid reaction medium comprising a substantially water-free alkyl nitrile selected from acetonitrile, propionitrile, butyronitrile, n-pentylnitrile, and cyclohexylnitrile.

12. A process according to claim 11 wherein the organic carboxylic acid ester is a glyceride ester selected from monoglyceride, diglyceride, and triglyceride esters of glycerol and $C_{10}$–$C_{20}$ organic carboxylic acids.

13. A process according to claim 12 wherein the glyceride ester is a triglyceride.

14. A process according to claim 11 wherein the alkyl nitrile is a member selected from the group consisting of acetonitrile and propionitrile.

15. A process according to claim 11 wherein the alkyl nitrile is acetonitrile and wherein the ester comprises the mixed glyceride esters derived from animal fats and oils or vegetable fats and oils.

16. A process according to claim 15 wherein the alkyl nitrile is acetonitrile and wherein the alkali metal hydroxide is sodium hydroxide.

* * * * *